United States Patent [19]

Foged et al.

[11] Patent Number: 6,015,544
[45] Date of Patent: Jan. 18, 2000

[54] PROCESS FOR PRODUCING RADIOLABELLED BENZODIAZEPINE RECEPTOR AGENTS AND COMPOSITION CONTAINING THE SAME

[75] Inventors: Christian Foged, Målov, Denmark; Christer Halldin, Stockholm, Sweden; Jukka Hiltunen, Tikkakoski, Finland; Lars Farde, Stockholm, Sweden

[73] Assignee: Map Medical Technologies Oy, Tikkakoski, Finland

[21] Appl. No.: 09/101,826

[22] PCT Filed: Mar. 18, 1997

[86] PCT No.: PCT/FI97/00177

§ 371 Date: Sep. 11, 1998

§ 102(e) Date: Sep. 11, 1998

[87] PCT Pub. No.: WO97/34898

PCT Pub. Date: Sep. 25, 1997

[30] Foreign Application Priority Data

Mar. 18, 1996 [FI] Finland ..................... 961246

[51] Int. Cl.[7] ............ A61K 51/00; A61M 36/14
[52] U.S. Cl. ............ 424/1.85; 424/1.11; 424/1.65; 424/1.81; 540/450; 548/100
[58] Field of Search ............ 424/1.11, 1.65, 424/1.81, 1.85, 1.89; 540/1, 450, 548, 498, 504, 500; 548/100, 300.1, 131, 143; 568/300; 514/220

[56] References Cited

U.S. PATENT DOCUMENTS

| | | | |
|---|---|---|---|
| 4,622,320 | 11/1986 | Wätjen et al. | 514/220 |
| 4,727,153 | 2/1988 | Watjen et al. | 548/131 |
| 4,745,112 | 5/1988 | Watjen et al. | 514/220 |
| 5,096,695 | 3/1992 | Carmann et al. | 424/1.11 |

FOREIGN PATENT DOCUMENTS

| | | |
|---|---|---|
| 0202441 | 11/1986 | European Pat. Off. . |
| 0226282 | 6/1987 | European Pat. Off. . |
| 0353754 | 2/1990 | European Pat. Off. . |

OTHER PUBLICATIONS

Foger et al., "Development of 123 I–labelled NNC 13–8241 as a Radioligand for SPECT, Visualization of Benzodiazepine Receptor Binding", *Nuclear Medicine & Biology*, vol. 23, No. 3, p. 202–209, (1996).

Kuikka et al., "Initial human studies with single–photon emission tomography using iodine–123 labelled 3-(5–cyclopropyl–1,2,4–oxadiazo–3–yl) 7–iodo–5,6–dihydro–5–methyl–6–0x0–4H–imidazo[1,5–a][1,4]–benzodiazepine (NNC 13–8241)", *European Journal of Nuclear Medicine*, vol. 23, No. 7, p. 798–803, (1996).

Kuikka et al., "Initial Human Studies with Spect Using [I–123] NNC 13–8241 for Visualization of Benzodiazepine Receptors.", *The Journal of Nuclear Medicine*, vol. 37, No. 5, p. 76–77, (1996).

Foged et al., "New Selective Radioligands for Examination of Benzodiazepine Receptors", *Journal of Nuclear Medicine*, vol. 34, No. 5, p. 89, (1993).

*Primary Examiner*—Jose' G. Dees
*Assistant Examiner*—Dameron Jones
*Attorney, Agent, or Firm*—Browdy and Neimark

[57] ABSTRACT

A process for producing a carrier free radio halogenated 3-(5-cyclopropyl-1,2,4-oxadiazol-3-yl)-5,6-dihydro-5-methyl-6-oxo-4H-imidazo[1,5-a][1,4]-benzodiazepine of formula (II) where $R^1$ is a radioactive halogen and $R^1$ may be at 7, 8, 9 or 10 substituent. The above compound is used in a pharmaceutical composition for nuclear medicine examination.

18 Claims, No Drawings

PROCESS FOR PRODUCING RADIOLABELLED BENZODIAZEPINE RECEPTOR AGENTS AND COMPOSITION CONTAINING THE SAME

This application is a 371 of PCT/FI97/00177 filed Mar. 18, 1997.

TECHNICAL FIELD

The present invention relates to a process for producing radioactive substituted benzodiazepines and to pharmaceutical compositions containing said benzodiazepines.

BACKGROUND ART

Radiolabelled compounds which are subject to localization in particular organs or tumors therein are of great value for the diagnosis of diseases of the human body. For example, iodine-123 labelled fatty acids and thallium-201 have been utilized as heart imaging agents. Various isonitrile ligands labelled with technetium-99m have been used to image infarcted regions on the heart.

Substituted benzodiazepines, which are labelled with iodine-123, iodine-125 or iodine-131 have been used for studies of benzodiazepine receptors in the brain.

A new benzodiazepine receptor ligand [radioiodine]3-(5-cyclopropyl-1,2,4-oxadiazol-3-yl)-7-iodo-5,6-dihydro-5-methyl-6-oxo-4H-imidazo[1,5-a][1,4]-benzodiazepine was introduced recently (C. Foged et al., J. Nucl Med. 1993: 34, p89).

The common preparation scheme for radioiodined carrier free neuroreceptor ligands employs a trialkyltin precursor and radioactive iodine by the chloramin-T method in strongly acidic conditions. However the labelling reaction is associated with a large and consistent formation of a radioactive volatile reaction product: methyliodine (Y. Zea-Ponce et al., J. Lab. Comp. Rad. 1994: 36, 331–337).

The side reaction products may contain up to 60% of the activity that is added into the reaction mixture. The loss of that amount of the activity increases production costs tremendously.

An another disadvantage, which results from the formation of methyliodine, is radio protection costs and problems. The high increase of the required radioactivity increases the need for radioprotection of persons in the very early moments during upscaling the process. Another radioprotection problem resides in the need to catch up methyliodine. Active charcoal filters, which are used to capture radioiodine from the air, do not hold methyliodine. It requires special reactor grade active charcoal filters that are another source of extra expenses.

DISCLOSURE OF THE INVENTION

To avoid the radioactive volatile by-product of the prior art we found an alternative route to produce [radiohalogenated]3-(5-cyclopropyl-1,2,4-oxadiazol-3-yl)-5,6-dihydro-5-methyl-6-oxo-4H-imidazo[1,5-a][1,4]-benzodiazepine (II).

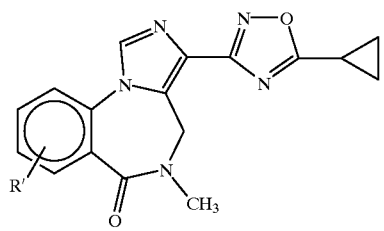

wherein R' is a radioactive halogen at position 7, 8, 9 or 10. Said radioactive halogen is preferably $123_I$, $124_I$, $125_I$, $131_I$. Other suitable radioactive halogens are $F^{18}$, $Br^{75}$, $Br^{76}$, $Br^{77}$.

The present invention is directed to a process for producing carrier free [radiohalogen]3-(5-cyclopropyl-1,2,4-oxadiazol-3-yl)-5,6-dihydro-5-methyl-6-oxo-4H-imidazo[1,5-a][1,4]-benzodiazepine using a halogenated precursor and HPLC purification with a high yield.

The present invention is also directed to a pharmaceutical composition containing said radiohalogenated benzodiazepine.

The process according to the present invention is defined in the appended claims. As described below, radioiodine is used as a non limiting example of radiohalogens.

According to the present invention formation of the radioactive methyliodine is avoided and the yield of the labelled benzodiazepine increases.

It is known that one can easily exchange a halogen on the benzene ring into another one having a lower atom number. In the opposite direction the reaction is rather slow and normally yields a poor result. Neuroreceptor imaging agents are required to be carrier free. The above mentioned exchange process results in a product having a carrier, where precursor and radiolabelled product are difficult to separate from each other.

The pharmaceutical composition according to the invention contains an effective amount of the compound (II) and a pharmaceutically acceptable liquid carrier material and optionally one or more pharmaceutically acceptable adjuvants. It is suitable for use as a benzodiazepine receptor imaging agent. In such medical use the radiohalogenated benzodiazepine is carrier free and an effective dose of the radiohalogenated benzodiazepine is generally about 20 to 1100 MBq preferably 37 to 370 MBq.

In the prior art processes the active ingredient in the final pharmaceutical composition binds to the walls of the glass vial. To prevent this unwanted binding on the walls of the glass vial, a solvent is added to the compound according to the present invention. The preferred solvents are such as ethanol, PEG, propyleneglycol, Tween or mixtures which contain two or more solvents, more preferably 1 to 20% by weight of ethanol.

In one embodiment of the present invention a preferred synthesis route comprises one wherein the halogen of 3-(5-cyclopropyl-1,2,4-oxadiazol-3-yl)-7-bromo-5,6-dihydro-5-methyl-6-oxo-4H-imidazo[1.5-a][1,4]-benzodiazepine is exchanged into radioactive iodine or the halogen of 3-(5-cyclopropyl-1,2,4-oxadiazol-3-yl)-7-iodo-5,6-dihydro-5-methyl-6-oxo-4H-imidazo[1,5-a][1,4]-benzodiazepine is exchanged into radioactive bromine or fluorine. The process is run at an elevated temperature and in a halogen-free acidic medium. The preferred temperature is 100° C. to 250° C. more preferably 130° C. to 200° C. most preferably 150–180° C. The radiolabelled compound is separated from the precursor using chromatographic methods. The preferred chromatographic method is HPLC and using a reversed phase column. The mobile phase comprises polar and non-polar solvents. The preferred mobile phase comprises 0.5:5 to 1:0.5 aqueous triethylamine and acetonitrile: It is more preferable that the mobile phase comprises 1:3 to 2:3 of 0.1–0.5% aqueous triethylamine (pH 3.5–9.5) and acetonitrile.

Chart 1

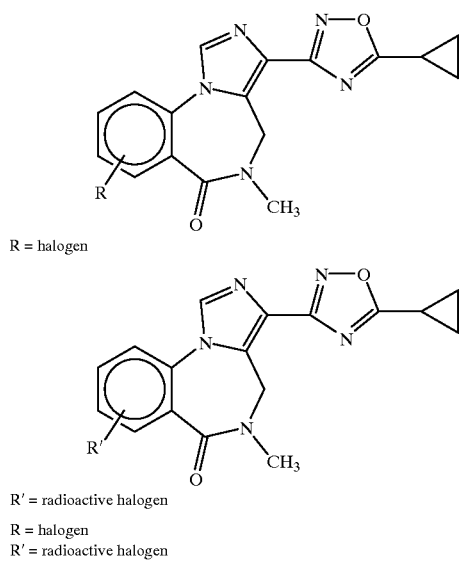

R = halogen

R' = radioactive halogen
R = halogen
R' = radioactive halogen

Experimental

The following experiments illustrate the invention, but they are not to be constructed as limiting the invention.

EXAMPLE 1

Synthesis of [$^{125}$I]3-(5-cyclopropyl-1,2,4-oxadiazol-3-yl)-7-iodo-5,6-dihydro-5-methyl-6-oxo-4H-imidazo[1,5-a][1,4]-benzodiazepine by replacing bromine with radioiodine starting from the bromo precursor 3-(5-cyclopropyl-1,2,4oxadiazol-3-yl)-7-bromo-5,6-dihydro-5-methyl-6-oxo-4H-imidazo[1,5-a][1,4]-benzodiazepine Na$^{125}$ (37 MBq in 10 µl) was dried in a gentle flow of nitrogen. 3-(5-cyclopropyl-1,2,4-oxadiazol-3-yl)-7-bromo-5,6-dihydro-5-methyl-6-oxo-4H-imidazo[1,5-a][1,4]-benzodiazepine in acetic acid (1 mg in 200 µl) was added to vial. The vial was heated at 150° C. for one hour. The acetic acid was then evaporated in a nitrogen flow and the residue was dissolved in a mobile phase (1 ml) and injected onto a HPLC µ-Bondapak-C-18 column. The mobile phase was 0.2% aqueous triethylamine (pH=7) and acetonitrile (3:5). The $^{125}$I-labelled product eluted with a retention time identical to that of a non-radioactive standard reference sample. The yield after purification was 45%, with a radiochemical purity of >98%.

EXAMPLE 2

Synthesis of [$^{123}$I]3-(5-cyclopropyl-1,2,4-oxadiazol-3-yl)-7-iodo-5,6-dihydro-5-methyl-6-oxo-4H-imidazo[1,5-a][1,4]-benzodiazepine by replacing bromine with radioiodine starting from the bromo precursor 3-(5-cyclopropyl-1,2,4-oxadiazol-3-yl)-7-bromo-5,6-dihydro-5-methyl-6-oxo-4H-imidazo[1,5-a][1,4]-benzodiazepine Na$^{123}$I (2200 MBq in 200 µl) was dried in a gentle flow of nitrogen. 3-(5-cyclopropyl-1,2,4-oxadiazol-3-yl)-7-bromo-5,6-dihydro-5-methyl-6-oxo-4H-imidazo[1,5-a][1,4]-benzodiazepine in acetic acid (0.35 mg in 70 µl) was added to a vial. The vial was heated at 160° C. for one and a half hours. The acetic acid was then evaporated and the residue was dissolved in a mobile phase (1 ml) and injected onto a HPLC µ-Bondapak-C-18 column. The mobile phase was 0.2% aqueous triethylamine (pH=7) and acetonitrile (2:3). The $^{123}$I-labelled product eluted with a retention time identical to that of a non-radioactive standard reference sample. The yield after purification was 75–80%, with a radiochemical purity of >98%.

EXAMPLE 3

The Effect of the Reaction Temperature on the Yield of Iodine-123 Labelled Benzodiazepine Example 2 was repeated to provide labelling as mentioned above except that the vial was heated to different temperatures as indicated in Table 1 below. The yield of labelled product was measured and the results are indicated in Table 1.

TABLE 1

Effect of the reaction temperature

| Temperature ° C. | [I-123]-benzodiazepine yield % |
|---|---|
| 100 | 10 |
| 150 | 40 |
| 165 | 80 |
| 200 | 70 |
| 250 | 60 |

The above experiment shows that an elevated temperature provides an increase in the yield of the radiolabelled benzodiazepine.

EXAMPLE 4

The Effect of Solvents on the Activity of the Product

The procedures of example 2 were repeated to provide labelled [$^{123}$I]3-(5-cyclopropyl-1,2,4-oxadiazol-3-yl)-7-iodo-5,6-dihydro-5-methyl-6-oxo-4H-imidazo[1,5-a][1,4]-benzodiazepine using a bromo precursor as described above. The resulting compounds were used to provide final pharmaceutical compositions using pharmaceutically acceptable buffers and solvents and 9 mg/ml sodium chloride as diluent. The product was incubated in a 10 ml glass vial over 24 hours. The labelled [$^{123}$I]benzodiazepine was drawn off. The residue activity in the vial was measured to find out how much of the reaction product had been bound to the glass walls of the vial. The procedure was repeated with different solvents and the results are disclosed in Table 2 below. The final concentration of the solvent must be pharmaceutically acceptable.

TABLE 2

| Solvent | Residue activity % of total activity |
| --- | --- |
| none | 20–35 |
| ethanol | 5–10 |
| glucose | 10–20 |
| Tween | 5–15 |
| PEG | 5–15 |
| glycerol | 5–15 |
| propylene glycol | 5–10 |
| ethanol-propylene | 5–10 |
| 30–70 | |

The experiments indicate that the use of suitable solvents will reduce the amount of compound bound to the walls of the reaction vessel and the product vial and therefore increase the over-all yield of the process.

EXAMPLE 5

Formulation of a Pharmaceutical Composition

The procedures of example 2 were repeated to provide labelled [$^{123}$I]3-(5-cyclopropyl-1,2,4-oxadiazol-3-yl)-7-iodo-5,6-dihydro-5-methyl-6-oxo-4H-imidazo[1,5-a][1,4]-benzodiazepine using a bromo precursor as described above. The resulting compounds were used to provide final pharmaceutical compositions using pharmaceutically acceptable buffers to get a final pH of 4.5 to 10 and solvents and 9 mg/ml sodium chloride as diluent. The following pharmaceutical composition was produced

| iodine 123-benzodiazepine | 185 | MBq | active ingredient |
| --- | --- | --- | --- |
| ethanol 94% | 0.5 | ml | solvent |
| 0,18 M NaH$_2$PO$_4$/Na$_2$HPO$_4$ pH 7 | 0.2 | ml | buffer |
| 9 mg/ml NaCl | 4.3 | ml | diluent |

The present invention has been described above with a reference to specific radiohalogenated benzodiazepines. A person skilled in the art will know, however, that similar procedures may be used to provide the other radiohalogenated compounds of the present invention.

We claim:

1. A process for producing a radiohalogenated 3-(5-cyclopropyl-1,2,4-oxadiazol-3-yl)-5,6-dihydro-5-methyl-6-oxo-4H-imidazo[1,5-a][1,4]-benzodiazepine wherein a precursor of the general formula (I)

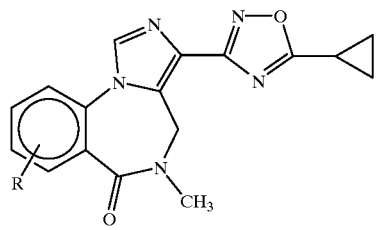

(I)

wherein R is bromine or iodine and R is a 7, 8, 9, or 10 substituent, is converted into a radiohalogenated 3-(5-cyclopropyl-1,2,4-oxadiazol-3-yl)-5,6-dihydro-5-methyl-6-oxo-4H-imidazo[1,5-a][1,4]-benzodiazepine of the general formula

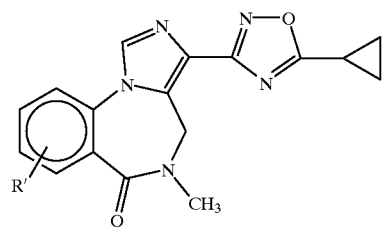

(II)

wherein R$^1$ is a radioactive halogen, selected from radioactive iodine, radioactive bromine, radioactive fluorine and R is a 7, 8, 9 or 10 substituent, by performing a radiohalogenization reaction comprising exchanging the inactive halogen of the precursor (I) into a radioactive halogen at an elevated temperature in a halogen-free acidic medium, whereafter the end product (II) is separated from the precursor (I) by using chromatographic methods.

2. A process for producing a radiohalogenated compound (II) according to claim 1 wherein said temperature is 100° C. to 250° C.

3. A process for producing a radiohalogenated compound (II) according to claim 1 wherein said chromatographic method is HPLC.

4. A process for producing a radiohalogenated compound (II) according to claim 1 wherein said chromatographic method is HPLC and a reversed phase column is used, the mobile phase comprising polar and nonpolar solvents.

5. A process for producing a radiohalogenated compound (II) according to claim 1 wherein said radioactive halogen is radioiodine.

6. A process for producing a radiohalogenated compound (II) according to claim 1 wherein said inactive halogen is bromine.

7. A process for producing a radiohalogenated compound (II) according to claim 1 wherein said radiohalogenated compound is radiolabelled 3-(5-cyclopropyl-1,2,4-oxadiazol-3-yl)-7-halogen-5,6-dihydro-5-methyl-6-oxo-4H-imidazo[1,5-a][1,4]-benzodiazepine.

8. The process according to claim 1, wherein the temperature is 130° C. to 200° C.

9. The process according to claim 1, wherein the temperature is 150° C. to 180° C.

10. The process according to claim 2, wherein said chromatographic method is HPLC.

11. The process according to claim 4, wherein the mobile phase of polar and nonpolar solvents comprises aqueous triethylamine and acetonitrile as a mixture in a ratio of 0.5:5 to 1:0.5 aqueous triethylamine at a pH of 3.5–9.5 to acetonitrile.

12. The process according to claim 11, wherein said ratio of aqueous triethylamine to acetonitrile is 1:3 to 2:3.

13. The process according to claim 2, wherein said inactive halogen is bromine.

14. The process according to claim 11, wherein said inactive halogen is bromine.

15. The process according to claim 14, wherein said radiohalogenated compound is radiolabelled 3-5 (-cyclopropyl-1,2,4-oxadiazol-3-yl)-7-halogen-5,6-dihydro-5-methyl-6-oxo-4H-imidaz [1,5-a] [1,4]-benzodiazepine.

16. The process according to claim 13, wherein said radiohalogenated compound is radiolabelled 3-5

(-cyclopropyl-1,2,4-oxadiazol-3-yl)-7-halogen-5,6-dihydro-5-methyl-6-oxo-4H-imidaz [1,5-a] [1,4]-benzodiazepine.

17. The process according to claim 11, wherein said radiohalogenated compound is radiolabelled 3-5 (-cyclopropyl-1,2,4-oxadiazol-3-yl)-7-halogen-5,6-dihydro-5-methyl-6-oxo-4H-imidaz [1,5-a] [1,4]-benzodiazepine.

18. The process according to claim 2, wherein said radiohalogenated compound is radiolabelled 3-5 (-cyclopropyl-1,2,4-oxadiazol-3-yl)-7-halogen-5,6-dihydro-5-methyl-6-oxo-4H-imidaz [1,5-a] [1,4]-benzodiazepine.

* * * * *